United States Patent
Jung et al.

(10) Patent No.: US 7,223,805 B2
(45) Date of Patent: May 29, 2007

(54) LIGHT-RESISTIVE DISPERSANT AND INK COMPOSITION CONTAINING THE SAME

(75) Inventors: Yeon-Kyoung Jung, Seoul (KR); Seung-min Ryu, Cycongi-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 178 days.

(21) Appl. No.: 10/724,753

(22) Filed: Dec. 2, 2003

(65) Prior Publication Data

US 2004/0139884 A1    Jul. 22, 2004

(30) Foreign Application Priority Data

Dec. 14, 2002   (KR) ..................... 10-2002-0080056

(51) Int. Cl.
*C08K 5/06*    (2006.01)
*C08K 5/13*    (2006.01)
*C09K 3/00*    (2006.01)

(52) U.S. Cl. ..................... 524/340; 524/385; 524/386; 252/385; 252/393; 106/31.27; 106/31.43; 106/31.51; 106/31.58; 106/31.75; 106/31.8; 106/31.86

(58) Field of Classification Search .............. 106/31.27, 106/31.43, 31.51, 31.58, 31.6, 31.75, 31.8, 106/31.86, 393; 524/340, 385, 386; 534/838; 546/329; 548/320.1; 558/194; 562/886; 564/170, 251; 252/385, 393
See application file for complete search history.

(56) References Cited

U.S. PATENT DOCUMENTS 6,346,595 B1    2/2002   O'Lenick, Jr.

*Primary Examiner*—Kriellion Sanders
(74) *Attorney, Agent, or Firm*—Staas & Halsey LLP

(57) ABSTRACT

A 2-methoxyphenol derivative may be used as an ultraviolet (UV) light absorbing dispersant and, an ink composition may include the 2-methoxyphenol derivative as a light-resistant dispersant. The 2-methoxyphenol derivative absorbs UV light and thus provides light resistance to outputs. The 2-methooxyphenol derivative also improves dispersibility. When the 2-methoxyphenol derivative is used to prepare an ink composition, the ink composition has improved dispersibility and light resistance, and there is no need to add a light-resistant additive.

18 Claims, No Drawings

LIGHT-RESISTIVE DISPERSANT AND INK COMPOSITION CONTAINING THE SAME

CROSS-REFERENCE TO RELATED APPLICATIONS

This application claims the priority of Korean Patent Application No. 2002-80056, filed on Dec. 14, 2002, in the Korean Intellectual Property Office, the disclosure of which is incorporated herein in its entirety by reference.

BACKGROUND OF THE INVENTION

1. Field of the Invention

The present invention relates to a light-resistant dispersant, and more particularly, to an ultraviolet (UV) light absorbing dispersant and an ink composition containing the same.

2. Description of the Related Art

In general, ink compositions for ink-jet printing contain a colorant, a solvent, and an additive, such as a dispersant. A dye or a pigment may be used for the colorant. However, when a dye is used as the colorant, water resistance and light resistance are limited, whereas when a pigment is used as the colorant, water resistance and light resistance are improved.

A common dispersant used in ink compositions is a polymer dispersant bearing hydrophilic and hydrophobic groups. The hydrophobic group of the polymer dispersant interacts with a colorant in the ink composition to stabilize dispersion of the colorant. The hydrophilic group of the polymer dispersant interacts with an aqueous solvent to offer steric stability.

However, due to the large molecular weight of the polymer dispersant, the physical properties, for example, the viscosity, of the composition are greatly varied even when there is a minor change in the amount of the dispersant. Accordingly, it is difficult to adjust the amount of the additive used. In addition, although the polymer dispersant includes hydrophilic groups in its molecular structure, the hydrophilic fraction of the polymer with respect to the total amount of the composition is too small to sufficiently dissolve the compound in water, and it takes more time to dissolve the hydrophilic fraction of the polymer.

After printing on media, such as paper, using the ink composition, the ink printed on the media is exposed to the air, moisture, and/or sunlight. Accordingly, an ink composition having effective light resistance and water resistance in such environments is required.

To improve the light resistance of ink compositions, a method of adding a silicon-containing compound as a light-resistant additive to offer a UV absorbing effect is suggested in U.S. Pat. No. 6,346,595. However, this silicone-containing compound is structurally complex, and thus has poor miscibility with other components of the ink composition, especially when it has a larger molecular weight.

SUMMARY OF THE INVENTION

The present invention provides a light-resistant dispersant providing an improved ultraviolet (UV) light absorbing property and dispersibility.

The present invention also provides an ink composition containing the above light-resistant dispersant, which has improved light resistance and dispersibility.

In one aspect, the present invention provides a 2-methoxyphenol derivative having formula (1) below:

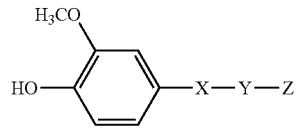

(1)

where X is selected from among a substituted or unsubstituted $C_1$–$C_{30}$ alkylene group, a substituted or unsubstituted $C_2$–$C_{30}$ alkenylene group, a substituted or unsubstituted $C_2$–$C_{30}$ alkynylene group, a substituted or unsubstituted $C_6$–$C_{30}$ arylene group, a substituted or unsubstituted $C_7$–$C_{30}$ arylalkylene group, a substituted or unsubstituted $C_1$–$C_{30}$ heteroalkylene group, a substitute or unsubstituted $C_2$–$C_{30}$ heteroarylene group, and a substituted or unsubstituted $C_3$–$C_{30}$ heteroarylalkylene group;

Y is selected from among —O—, —NR—, —N(H)=N(H)—, —S—, —P—, —C(=O)—NR—, —NR—C(=O)—, —S(=O)(=O)O—, —C(=O)O—, —O—C(=O)—, —P(=O)O—, —C(=O)—O—C(=O)—, —C(=O)—S—C(=O)—, —C(=O)—NR—C(=O)—, —C(=NH)—O—C(=NH)—, —C(=S)—O—C(=S)—, —C(=NH)—NR—C(=NH)—, —C(=S)—NR—C(=S)—, —C(=NH)—S—C(=NH)—, and —C(=S)—S—C(=S)—, where R is a hydrogen atom or a $C_1$–$C_5$ alkyl group; and Z is one of a group having the formula of —$(CH_2CH_2O)_a$—$(CH_2CH(CH_3)O)_b$—$(CH_2CH_2O)_c$—H where a, b, and c are independently integers from 1 to 20 and a group having formula (2) below:

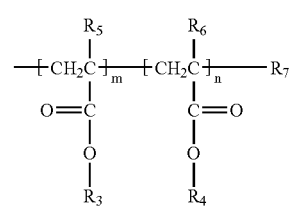

(2)

where $R_3$ and $R_4$ are independently $C_1$–$C_{10}$ alkyl groups; $R_5$ and $R_6$ are independently a hydrogen atom or a methyl group; $R_7$ is selected from among a $C_1$–$C_{30}$ alkylene group, a $C_2$–$C_{30}$ alkenylene group, $C_2$–$C_{30}$ alkynylene group, a $C_6$–$C_{30}$ arylene group, a $C_7$–$C_{30}$ arylalkylene group, a $C_1$–$C_{30}$ heteroalkylene group, a $C_2$–$C_{30}$ heteroarylene group, and a $C_3$–$C_{30}$ heteroarylalkylene group, which have a terminal group selected from among a phosphoric acid or a salt thereof, a phosphoric acid or a salt thereof, a sulfonic acid or a salt thereof, —OH, and —$NH_2$; and m and n are independently real numbers from 1 to 10 where m+n≧2.

In another aspect, the present invention provides an ink composition containing the 2-methoxyphenol derivative of formula (1), an aqueous medium, and a colorant. The amount of the 2-methoxyphenol derivative may be in the range of 0.1–20 parts by weight with respect to 100 parts by weight of the ink composition.

DETAILED DESCRIPTION OF THE PREFERRED EMBODIMENTS

A 2-methoxyphenol derivative having formula (1) according to an embodiment of the present invention will be described in detail.

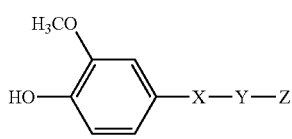

(1)

In formula (1) above, the 2-methoxyphenol ring and X are anchoring groups that improve reactivity, for example, chemical affinity, with a pigment used as a colorant, Y is a junction group, and Z is a stabilizing group that facilitates dispersion of a pigment in a solvent.

X in formula (1) is selected from among a substituted or unsubstituted $C_1$–$C_{30}$ alkylene group, a substituted or unsubstituted $C_2$–$C_{30}$ alkenylene group, a substituted or unsubstituted $C_2$–$C_{30}$ alkynylene group, a substituted or unsubstituted $C_6$–$C_{30}$ arylene group, a substituted or unsubstituted $C_7$–$C_{30}$ arylalkylene group, a substituted or unsubstituted $C_1$–$C_{30}$ heteroalkylene group, a substitute or unsubstituted $C_2$–$C_{30}$ heteroarylene group, and a substituted or unsubstituted $C_3$–$C_{20}$ heteroarylalkylene group.

Examples of an unsubstituted $C_1$–$C_{30}$ alkylene group for X in formula (1) include, but are not limited to, a methylene group, an ethylene group, a propylene group, an isopropylene group, a sec-butylene group, a pentylene group, an iso-amylene group, and a hexylene group, wherein at least one hydrogen atom in the alkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_2$–$C_{20}$ alkenyl group, a $C_2$–$C_{20}$ alkynyl group, a $C_1$–$C_{20}$ heteroalkyl group, a $C_6$–$C_{20}$ aryl group, a $C_7$–$C_{20}$ arylalkyl group, a $C_2$–$C_{20}$ heteroaryl group, or a $C_3$–$C_{20}$ heteroarylalkyl group.

An unsubstituted $C_2$–$C_{30}$ alkenylene or alkynylene group for X in formula (1) includes a carbon double or triple bond in the middle or at the end of the alkylene group defined above. Examples of such an unsubstituted $C_1$–$C_{30}$alkenylene or alkynylene group include ethylene, propylene, butylene, hexylene, acetylene, and the like. At least one hydrogen atom in the alkenylene or alkynylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_2$–$C_{20}$ alkenyl group, a $C_2$–$C_{20}$ alkynyl group, a $C_1$–$C_{20}$ heteroalkyl group, a $C_6$–$C_{20}$ aryl group, a $C_7$–$C_{20}$ arylalkyl group, a $C_2$–$C_{20}$ heteroaryl group, or a $C_3$–$C_{20}$ heteroarylalkyl group.

A heteroalkylene group for X in formula (1) includes a nitrogen atom, sulfur atom, oxygen atom, or phosphorous atom in the alkylene group defined above. Examples of such a heteroalkylene group include a methoxy group, an ethoxy group, a propoxy group, a butoxy group, a t-butoxy group, and the like. Examples of a heteroalkylene group with a substituent include haloalkoxy radicals, such as fluoromethoxy, chloromethoxy, trifluoromethoxy, trifluoroethoxy, fluoroethoxy, fluoropropoxy, and the like. At least one hydrogen atom in the heteroalkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$alkynyl group, a $C_1$–$C_{20}$ heteroalkyl group, a $C_6$–$C_{20}$ aryl group, a $C_7$–$C_{20}$ arylalkyl group, a $C_6$–$C_{20}$ heteroaryl group, or a $C_6$–$C_{20}$ heteroarylalkyl group.

An arylene group for X in formula (1), which may be used alone or in combination, refers to a $C_6$–$C_{30}$ carbocyclic system containing at least one ring wherein such rings may be attached together in a pendent manner or may be fused. The term "aryl" implies aromatic radicals, such as phenyl, naphthyl, tetrahydronaphthyl, indane, biphenyl, and the like. The arylene group may have a substituent, such as hydroxy, halo, haloalkyl, nitro, cyano, alkoxy, lower alkylamino, and the like. At least one hydrogen atom in the arylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$alkenyl group, a $C_1$–$C_{20}$ alkynyl group, a $C_1$–$C_{20}$ heteroalkyl group, a $C_6$–$C_{20}$ aryl group, a $C_7$–$C_{20}$ arylalkyl group, a $C_6$–$C_{20}$ heteroaryl group, or a $C_6$–$C_{20}$ heteroarylalkyl group.

An arylalkylene group for X in formula (1) refers to the above-defined arylene group having lower alkyl substitute radicals, for example, methyl, ethyl, propyl, and the like, for some hydrogen atoms. Examples of such an arylalkylene group include benzyl, phenylethyl, etc. At least one hydrogen atom in the arylalkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$ alkynyl group, a $C_1$–$C_{20}$ heteroalkyl group, a $C_6$–$C_{20}$ aryl group, a $C_7$–$C_{20}$ arylalkyl group, a $C_6$–$C_{20}$ heteroaryl group, or a $C_6$–$C_{20}$ heteroarylalkyl group.

A heteroarylene group for X in formula (1) refers to a divalent cyclic system containing one, two, or three hetero atoms selected from the group consisting of N, O, P, and S. At least one hydrogen atom in the heteroarylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_2$–$C_{20}$ alkenyl group, a $C_2$–$C_{20}$ alkynyl group, a $C_1$–$C_{20}$ heteroalkyl group, a $C_6$–$C_{20}$ aryl group, a $C_7$–$C_{20}$ arylalkyl group, a $C_6$–$C_{20}$ heteroaryl group, or a $C_7$–$C_{20}$ heteroarylalkyl group.

A heteroarylalkylene group for X in formula (1) refers to the above-defined heteroarylene group having alkylene groups. At least one hydrogen atom in the heteroarylalkylene group may be substituted with a halogen atom, a hydroxy group, a nitro group, a cyano group, an amino group, an amidino group, hydrazine, hydazone, a carboxyl group or a salt thereof, a sulfonic acid group or a salt thereof, a phosphoric acid group or a salt thereof, a $C_1$–$C_{20}$ alkyl group, a $C_1$–$C_{20}$ alkenyl group, a $C_1$–$C_{20}$ alkynyl group, a $C_1$–$C_{20}$ heteroalkyl group, a $C_6$–$C_{20}$ aryl group, a $C_7$–$C_{20}$ arylalkyl group, a $C_6$–$C_{20}$ heteroaryl group, or a $C_6$–$C_{20}$ heteroarylalkyl group.

In formula (1) above, Y is selected from among —O—, —NR—, —N(H)=N(H)—, —S—, —P—, —C(=O)—NR—, —NR—C(=O)—, —S(=O)(=O)O—, —C(=O)O—, —O—C(=O)—, —P(=O)O—, —C(=O)—O—C(=O)—, —C(=O)—S—C(=O)—, —C(=O)—N R—C(=O)—, —C(=NH)—O—C(=NH)—, —C(=S)—O—C(=S)—, —C=(NH)—NR—C(=NH)—, —C(=S)—

NR—C(=S)—, —C(=NH)—S—C(=NH)—, and —C(=S)—S—C(=S)—, where R is a hydrogen atom or a $C_1$–$C_5$ alkyl group.

In formula (1) above, Z is one of a group having the formula of —$(CH_2CH_2O)_a$—$(CH_2CH(CH_3)O)_b$—$(CH_2CH_2O)_c$—H where a, b, and c are independently integers from 1 to 20 and a group having formula (2) below:

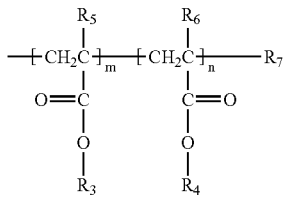

(2)

where $R_3$ and $R_4$ are different $C_1$–$C_{10}$ alkyl groups; $R_5$ and $R_6$ are independently a hydrogen atom or a methyl group; $R_7$ is selected from among a $C_1$–$C_{30}$ alkylene group, a $C_2$–$C_{30}$ alkenylene group, $C_2$–$C_{30}$ alkynylene group, a $C_6$–$C_{30}$ arylene group, a $C_7$–$C_{30}$ arylalkylene group, a $C_1$–$C_{30}$ heteroalkylene group, a $C_2$–$C_{30}$ heteroarylene group, and a $C_3$–$C_{30}$ heteroarylalkylene group, which have a terminal group selected from among a carboxylic acid or a salt thereof, a phosphoric acid or a salt thereof, a sulfonic acid or a salt thereof, —OH, and —$NH_2$; and m and n are real numbers from 1 to 10 where m+n≧2.

The 2-methoxyphenol derivative of formula (1) according to an embodiment of the present invention absorbs UV light and provides dispersibility. Accordingly, when 2-methoxyphenol is added to an ink composition, the light resistance and dispersibility of the ink composition are improved.

An ink composition according to an embodiment of the present invention that contains the above-described 2-methoxyphenol derivative of formula (1) will now be described in detail.

An ink composition according to an embodiment of the present invention includes an aqueous medium, a colorant, and the 2-methoxyphenol derivative of formula (1) acting as a light-resistant dispersant. The ink composition according to an embodiment of the present may contain 0.1–20 parts by weight of the compound of formula (1) with respect to 100 parts by weight of the ink composition.

Water may be used alone for the aqueous medium of the ink composition according to an embodiment of the present invention. Alternatively, a mixture of water and at least one organic solvent may be used for the aqueous medium. In this case, the amount of the organic solvent may be in the range of 2–50 parts by weight with respect to 100 parts by weight of the aqueous medium. The viscosity and surface tension of the ink composition may be adjusted within an appropriate range using an organic solvent in the aqueous medium.

Examples of the organic solvent include, but are not limited to, alcohols, such as methyl alcohol, ethyl alcohol, n-propyl alcohol, isopropyl alcohol, n-butyl alcohol, sec-butyl alcohol, t-butyl alcohol, isobutyl alcohol, etc.; ketones, such as acetone, methylethyl ketone, diacetone alcohol, etc.; esters, such as ethyl acetate, ethyl lactate, etc.; polyhydric alcohols, such as ethylene glycol, diethylene glycol, triethylene glycol, propylene glycol, butylene glycol, 1,4-butane diol, 1,2,4-butane triol, 1,5-pentane diol, 1,2-hexane diol, 1,6-hexane diol, 1,2,6-hexane triol, hexylene glycol, glycerol, glycerol ethoxylate, trimethylolpropane ethoxylate, etc.; lower alkyl ethers, such as ethylene glycol monomethyl ether, ethylene glycol monoethyl ether, diethylene glycol methyl ether, diethylene glycol ethyl ether, diethylene glycol methyl ether, diethylene glycol ethyl ether, triethylene glycol monomethyl ether, triethylene glycol monoethyl ether, etc.; nitrogen-containing compounds, such as 2-pyrrolidone, N-methyl-2-pyrrolidone, caprolactam, etc.; and sulfur-containing compounds, such as dimethyl sulfoxide, tetramethylene sulfone, thioglycol, etc.

The ink composition according to an embodiment of the present invention may further include an additive, for example, a viscosity adjuster, a surfactant, a storage stabilizer, or a wetting agent.

The viscosity adjuster of the ink composition ensures a smoother jetting process through viscosity adjustment. Examples of the viscosity adjuster that may be used in an embodiment of the present invention include polyvinyl alcohol, casein, carboxymethylcellulose, etc. The amount of the viscosity adjuster may be in the range of 0.1–5.0 parts by weight with respect to 100 parts by weight of the total weight of 2-methoxy phenol derivative, an aqueous medium, and a colorant.

The surfactant of the ink composition controls the surface tension of the ink composition. An anionic surfactant, cationic surfactant or a nonionic surfactant may be used for the surfactant. In particular, the surfactant of the ink composition stabilized wettability when the composition is sprayed via a nozzle. The amount of the surfactant may be in the range of 0.1–5.0 parts by weight with respect to 100 parts by weight of the ink composition.

The wetting agent of the ink composition prevents nozzles from being clogged with the ink composition. Examples of the wetting agent include polyhydric alcohols, in particular, glycerin, ethylene glycol, diethylene glycol, triethylene glycol, propylene glycol, dipropylene glycol, hexylene glycol, 1,3-butanediol, 1,4-butanediol, 1,5-pentanediol, 1,2-hexanediol, 1,6-hexanediol, 2-butene-1,4-diol, 2-methyl-2-pentanediol, and a mixture of the foregoing alcohols. The amount of the wetting agent may be in the range of 2–40 parts by weight with respect to 100 parts by weight of the total weight of 2-methoxy phenol derivative, an aqueous medium, and a colorant.

The ink composition according to an embodiment of the present invention uses a disperse dye or pigment for the colorant. Specific examples of the disperse dye include, but are not limited to, DISPERSE YELLOW 3, DISPERSE YELLOW 54, DISPERSE YELLOW 82, DISPERSE RED 60, DISPERSE RED 375, DISPERSE VIOLET 17, DISPERSE RED 4, DISPERSE RED 11, DISPERSE BLUE 60, DISPERSE BLUE 359, DISPERSE BLUE 14, DISPERSE BLUE 3, DISPERSE BLUE 72, DISPERSE BLUE 56. Specific examples of the pigment include, but are not limited to, carbon black, graphite, vitreous carbon, activated charcoal, activated carbon, anthraquinone, phthalocyanine blue, phthalocyanine green, diazos, monoazos, pyranthrones, perylene, quinacridone, and indigoid pigments.

The amount of the colorant may be in the range of 0.1–20 parts by weight, preferably, 0.5–15 parts by weight, with respect to 100 parts by weight of the ink composition.

The ink composition of an embodiment of the present invention may further include an acid or a base to increase the solubility of the dispersant in a solvent and stabilize the dispersion of the pigment.

The above ink composition according to an embodiment of the present invention may be prepared as follow. Initially, the 2-methoxyphenol derivative of formula (1) above acting as a light-resistant dispersant, a colorant, and additionally additives such as a viscosity adjuster and a surfactant are added to an aqueous medium and thoroughly mixed using a stirrer to homogenize. The resultant mixture is passed through a filter to provide an ink composition according to an embodiment of the present invention.

The 2-methoxyphenol derivative of formula (1) according to an embodiment of the present invention may be used for, but is not limited to, toner compositions, various paints, coating solutions, and the like, in addition to ink compositions.

The present invention will be described in greater detail with reference to the following examples. The following examples are for illustrative purposes and are not intended to limit the scope of the invention. Although the following examples are described with reference to ink compositions containing the 2-methoxyphenol derivative of formula (1), it will be appreciated that the present invention is not limited to the ink compositions recited and that experimental methods used to evaluate the properties of the ink compositions may be applied to wet toners, dry toners, paints, and coating solutions.

SYNTHETIC EXAMPLE 1

16.42 g of 2-methoxy-4-(1-prophenyl)phenol and 16.40 g of an alkoxylated alcohol having formula (3) below were reacted in the presence of an acidic or basic catalyst to provide 22.97 g of a compound having formula (4) below.

$$HO-CH_2CH_2O-CH_2CH(CH_3)O-CH_2CH_2OH \quad (3)$$

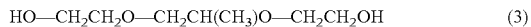

(4)

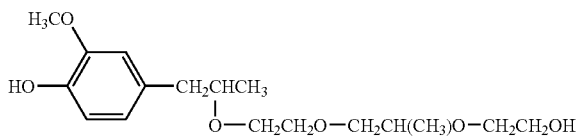

SYNTHESIS EXAMPLE 2

11.81 g of succinic acid was reacted with 16.40 g of the alkoxylated alcohol having formula 3 above in the presence of an acidic catalyst (HCl or $H_2SO_4$). 18.96 g of 4-hydroxy-3-methoxybenzylamine hydrochloride was added to the reaction product and reacted in the presence of $SOCl_2$ to provide 28.12 g of a compound having formula (5) below.

(5)

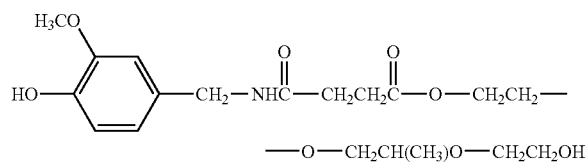

SYNTHESIS EXAMPLE 3

11.81 g of succinic acid was reacted with 16.40 g of the alkoxylated alcohol having formula 3 above in the presence of an acidic catalyst (HCl or $H_2SO_4$). 18.02 g of 4-(3-hydroxyl-1-propenyl)-2-methoxyphenol was added to the reaction product and reacted in the presence of an acidic catalyst to provide 29.83 g of a compound having formula (6) below.

(6)

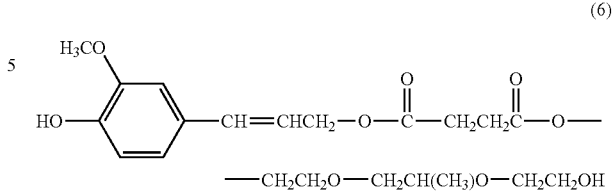

SYNTHESIS EXAMPLE 4

(1) 100 mL of chloroform was placed in a 250-mL round-bottomed flask and bubbled while supplying a HCl gas for 1–2 hours. 29.5 g of 2-methoxy-4-(2-propenyl)phenol was added into the flask, refluxed for 6 hours or longer, and concentrated to provide 27.5 g of a crystalline compound (A).

(2) 6.9 g of the crystalline compound (A) was dissolved in 100 mL of dimethylsulfoxide (DMSO). 37.3 g of an alkoxylated alcohol having formula (7) below was added to the solution, reacted at 120° C. for 8 hours or longer, and concentrated to provide a solution (B). This solution (B) was dissolved in ether and washed with distilled water several times to extract the ether phase. This ether phase was reconcentrated to provide 22.2 g of a compound having formula (8) below.

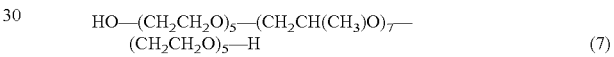

(8)

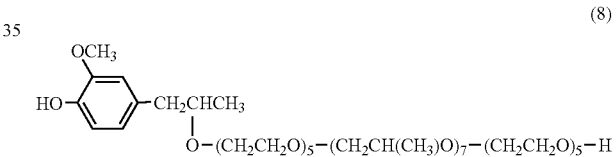

SYNTHESIS EXAMPLE 5

(1) 129.6 g of the alkoxylated alcohol of formula (7) above and 17.8 g of succinic acid were dissolved in 150 mL of ethyl acetate contained in a 250-mL round-bottomed flask. 30 mL of concentrated sulfuric acid was slowly added together with one or two boiling chips into the solution and refluxed for 12 hours or longer. The reaction solution was washed with distilled water to extract the organic phase. This organic phase was concentrated to provide 88.4 g of a crystalline compound (C).

(2) 4.6 g of 4-hydroxyl-3-methoxybenzylamine hydrochloride and 3.3 g of $SOCl_2$ were dissolved in 50 mL of DMSO contained in a 250-mL Erlenmeyer flask and reacted at room temperature for 3 hours or longer to provide a solution (D). A solution of 27.6 g of the crystalline compound (C) in 100 mL of DMSO was added to the solution (D) together with one or two boiling chips and refluxed for 6 hours or longer.

The reaction solution was cooled to room temperature, and excess methanol was added to precipitate a crystalline compound (E), followed by suction filtration. To remove the unreacted reactant, the crystalline compound (E) was dissolved in DMSO, and methanol was added to the solution to precipitate it again. The precipitant was collected using a suction filter and dried in an oven to provide 15.2 g of a compound having formula (9) below.

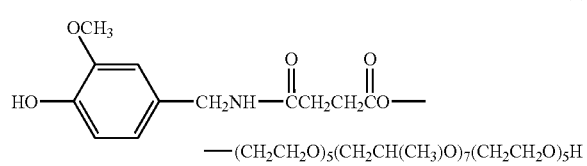

(9)

SYNTHESIS EXAMPLE 6

4.3 g of 4-(3-hydroxyl-1-propenyl)-2-methoxyphenol and 27.1 g of the crystalline compound (C) obtained in Synthesis Example 5 were dissolved in 100 mL of ethyl acetate contained in a 250-mL round-bottomed flask. 15 mL of concentrated sulfuric acid was slowly added together with one or two boiling chips into the solution and refluxed for 10 hours or longer. The reaction solution was washed with distilled water to extract the organic phase. This organic phase was concentrated to provide 13.7 g of a compound having formula (10) below.

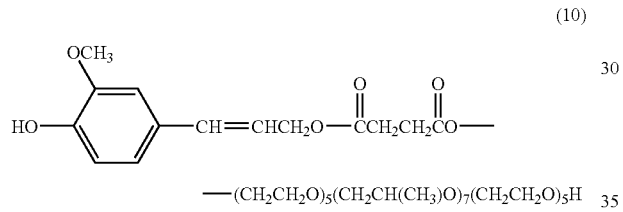

(10)

SYNTHESIS EXAMPLE 7

17.5 g of a compound having formula (12) was synthesized in the same manner as in (2) of Synthesis Example 4, except that 31.9 g of an alkoxylated alcohol having formula (11) below and 7.2 g of the crystalline compound (A) obtained in Synthesis Example 4 were used.

$$HO—(CH_2CH_2O)_3—(CH_2CH(CH_3)O)_4—(CH_2CH_2O)_8—H \qquad (11)$$

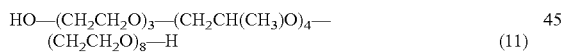

(12)

SYNTHESIS EXAMPLE 8

(1) 78.2 g of a crystalline compound (F) was synthesized in the same manner as in (1) of Synthesis Example 5, except that 112.3 g of the alkoxylated alcohol of formula (11) above and 18.1 g of succinic acid were used.

(2) 12.5 g of a compound having formula (13) below was synthesized in the same manner as in Synthesis Example 6, except that 4.3 g of 4-(3-hydroxyl-1-propenyl)-2-methoxyphenol and 23.4 g of the crystalline compound (F) were used.

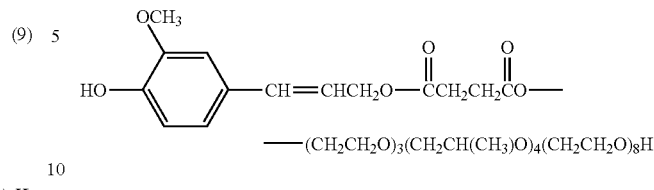

(13)

SYNTHESIS EXAMPLE 9

22.5 g of an acrylate copolymer (having a weight average molecular weight of 1500) having formula (14) below and 2.7 g of 4-(3-hydroxyl-1-propenyl)-2-methoxyphenol were dissolved in 50 mL of ethyl acetate contained in a 100-mL round-bottomed flask. 7 mL of concentrated sulfuric acid was slowly dropped together with one or two boiling chips into the solution and refluxed for 12 hours or longer.

The resulting reaction solution was slowly added to 50 mL of ether contained in a 200-mL Erlenmeyer flask to precipitate a crystalline compound. This crystalline compound was collected using a suction filter and dried to provide 13.5 g of a compound having formula (15) below. In formula (14) below, m=9 and n=4.5.

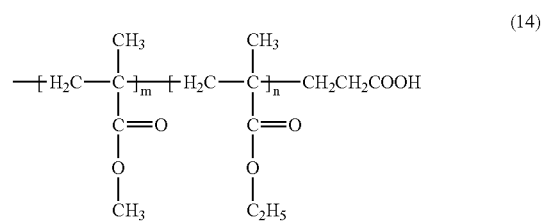

(14)

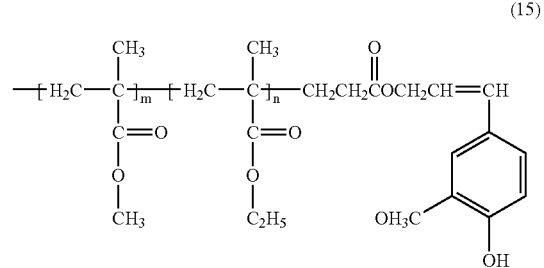

(15)

SYNTHESIS EXAMPLE 10

24.2 g of the crystalline compound (F) obtained in (1) of Synthesis Example 8 was dissolved in 50 mL of DMSO contained in a 250-mL Erlenmeyer flask. 5.2 g of $SOCl_2$ was added to the solution and reacted at room temperature for 1 hour or longer to provide a solution (G). A solution of 5.8 g of a 2-methoxyphenol derivative having formula (16) below in 50 mL of DMSO was added to the solution (G) together with one or two boiling chips and refluxed at 80° C. for 6 hours or longer. The resulting reaction solution was cooled to room temperature, and excess methanol was added to precipitate a crystalline compound, followed by suction filtration. To remove the unreacted reactant, the crystalline compound was dissolved in DMSO, and methanol was added to the solution to precipitate it again. The precipitant was collected using a suction filter and dried to provide 16.8 g of a compound having formula (17) below.

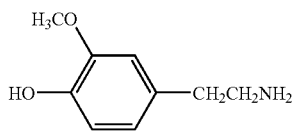

(16)

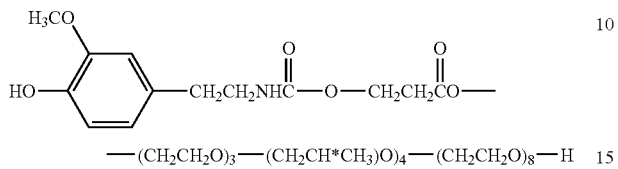

(17)

SYNTHESIS EXAMPLE 11

18.2 g of a compound having formula (19) below was synthesized in the same manner as in Synthesis Example 10, except that 27.0 g of the crystalline compound (C) obtained in Synthesis Example 5 and 7.8 g of a 2-methoxyphenol derivative having formula (18) below were used.

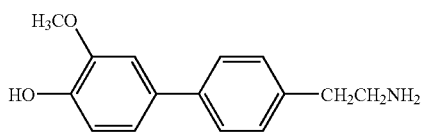

(18)

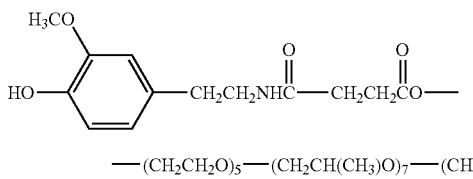

(19)

SYNTHESIS EXAMPLE 12

16.1 g of a compound having formula (21) below was synthesized in the same manner as in Synthesis Example 6, except that 23.4 g of the crystalline compound (F) obtained in (1) of Synthesis Example 8 and 7.1 g of a 2-methoxyphenol derivative having formula (20) below were used.

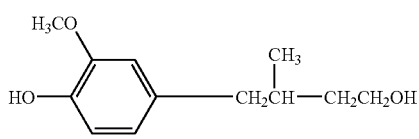

(20)

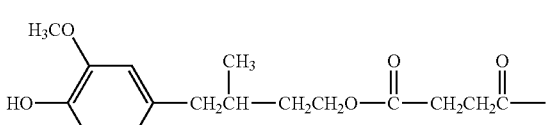

(21)

SYNTHESIS EXAMPLE 13

15.6 g of a compound having formula (23) below was synthesized in the same manner as in Synthesis Example 6, except that 7.6 g of a 2-methoxyphenol derivative having formula (22) below and 22.0 g of the alkoxylated alcohol of formula (11) above were used.

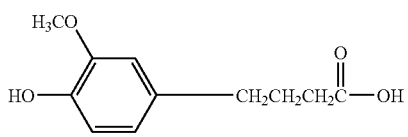

(22)

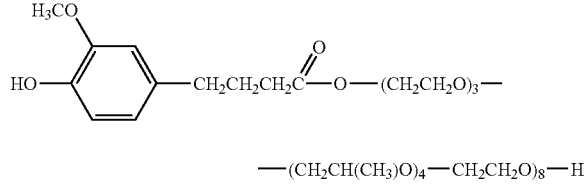

(23)

SYNTHESIS EXAMPLE 14

15.6 g of a compound having formula (24) below was synthesized in the same manner as in Synthesis Example 9, except that 2.9 g of the 2-methoxyphenol derivative having formula (16) above and 22.5 g of the acrylate copolymer having formula (14) above were used. In formula (24) below, $m=9$, and $n=4.5$.

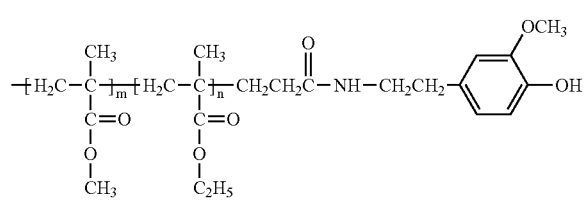

(24)

EXAMPLE 1

The following components were mixed while stirring for 30 minutes or longer to homogenize. The mixture was passed through a filter to provide an ink composition.

| COMPONENT | CONTENT |
|---|---|
| Colorant (Carbon black) | 4.0 g |
| Water | 73.0 g |
| Isopropyl alcohol | 3.0 g |
| Glycerin | 8.0 g |
| Ethylene glycol | 8.0 g |
| Compound of formula 4 | 4.0 g |

EXAMPLES 2–14

Ink compositions were prepared in the same manner as in Example 1, except that the compounds of formulae (5), (6), (8), (9), (10), (12), (13), (15), (17), (19), (21), (23), and (24) were respectively used instead of the compound of formula (4).

COMPARATIVE EXAMPLES 1–5

Ink compositions were prepared in the same manner as in Example 1, except that TEGO dispers 750W, TEGO wet 260, a styrene-acrylic acid copolymer, arylamine/styrene-sulfonic acid copolymer, and a 4-vinylpyrridine/maleic acid copolymer were respectively used instead of the compound of formula (4), 0.5 g of IRGANOX 245DW (available from CIBA CO.) was further added, and the amount of water was reduced by 0.5 g.

The properties of the ink compositions prepared in Examples 1 through 14 and Comparative Examples 1 through 5 were evaluated as follows.

(1) Storage Stability 100 mL of samples of the ink compositions prepared in Examples 1 through 14 and Comparative Examples 1 through 5 were portioned into respective heat-resistant glass bottles. The glass bottles were sealed and stored in a 60° C.-convection oven for 2 months. It was observed whether precipitates appeared in the bottles. The results are shown in Table 1. In Table 1, O indicates that no precipitate appears, and X indicates that precipitates appear.

(2) Light Resistance

Ink cartridges (available from SAMSUNG ELECTRONICS CO.) were filled with the respective ink compositions of Examples 1 through 14 and Comparative Examples 1 through 5. After printing 2×2 cm solid patterns using the ink cartridges, the printed results were exposed to light for 100 hours in a Q-SUN XENON TEST CHAMBER. Optical density (OD) was measured before and after light exposure, and A values were calculated using the following equation. Light resistance was evaluated as good (O) for A 90, moderate (Δ) for 75 A<90, and poor (X) for A<75. The results are shown in Table 2.

$A = OD$ after test/$OD$ before test×100(%)

improved dispersibility and light resistance, and there is no need to add a light-resistant additive.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A composition comprising:
a 2-methoxyphenol derivative having formula (1) below:

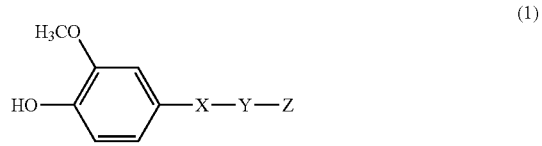

(1)

where X is an unsubstituted $C_1$–$C_{30}$ alkylene;
Y is —O—;
Z is selected from the group having the formula of
—$(CH_2CH_2O)_a(CH_2CH(CH_3)O)_b(CH_2CH_2O)_c$—H
where a, b, and c are less than 10;
a functional aqueous medium that is water; and
a functional colorant that is a carbon black pigment.

2. The composition of claim 1, wherein an amount of the 2-methoxyphenol derivative is in a range of 0.1–20 parts by weight with respect to 100 parts by weight of the composition.

3. The composition according to claim 1, further including at least one of: a viscosity adjuster, a surfactant, a storage stabilizer, and a wetting agent.

4. The composition according to claim 3, wherein the viscosity adjuster includes at least one of: polyvinyl alcohol, casein, and carboxymethylcellulose.

TABLE 1

|  | Example | | | | | | | | | | | | | | Comparative Example | | | | |
| --- | --- | --- | --- | --- | --- | --- | --- | --- | --- | --- | --- | --- | --- | --- | --- | --- | --- | --- | --- |
| No. | 1 | 2 | 3 | 4 | 5 | 6 | 7 | 8 | 9 | 10 | 11 | 12 | 13 | 14 | 1 | 2 | 3 | 4 | 5 |
| Result | O | O | O | O | O | O | O | O | O | O | O | O | O | O | X | X | X | X | X |

TABLE 2

|  | Example | | | | | | | | | | | | | | Comparative Example | | | | |
| --- | --- | --- | --- | --- | --- | --- | --- | --- | --- | --- | --- | --- | --- | --- | --- | --- | --- | --- | --- |
| No. | 1 | 2 | 3 | 4 | 5 | 6 | 7 | 8 | 9 | 10 | 11 | 12 | 13 | 14 | 1 | 2 | 3 | 4 | 5 |
| Result | O | O | O | O | O | O | O | O | O | O | O | O | O | O | Δ | Δ | O | Δ |

As described above, a 2-methoxyphenol derivative having formula (1) above according to an embodiment of the present invention absorbs UV light and thus provides light resistance to outputs. In addition, the 2-methoxyphenol derivative improves dispersibility. Therefore, the compound of formula (1) is used as a light-resistant dispersant in ink compositions. When the 2-methoxyphenol derivative is used to prepare an ink composition, the ink composition has 5. The composition according to claim 4, wherein an amount of the viscosity adjuster is in a range of 0.1–5.0 parts by weight with respect to 100 parts by weight of a total weight of the 2-methoxy phenol derivative, the aqueous medium, and the colorant.

6. The composition according to claim 3, wherein the surfactant is one of: an anionic surfactant, a cationic surfactant and a nonionic surfactant.

7. The composition according to claim 6, wherein an amount of the surfactant is in a range of 0.1–5.0 parts by weight with respect to 100 parts by weight of the composition.

8. The composition according to claim 3, wherein the wetting agent of the composition includes at least one of: polyhydric alcohols, in particular, glycerin, ethylene glycol, diethylene glycol, triethylene glycol, propylene glycol, dipropylene glycol, hexylene glycol, 1,3-butanediol, 1,4-butanediol, 1,5-pentanediol, 1,2-hexanediol, 1,6-hexanediol, 2-butene-1,4-diol, 2-methyl-2-pentanediol, and a mixture of the foregoing alcohols.

9. The composition according to claim 8, wherein an amount of the wetting agent is in a range of 2–40 parts by weight with respect to 100 parts by weight of the total weight of 2-methoxy phenol derivative, an aqueous medium, and a colorant.

10. The composition according to claim 1, wherein the colorant includes a disperse dye or pigment.

11. The composition according to claim 10, wherein the disperse dye is at least one of: DISPERSE YELLOW 3, DISPERSE YELLOW 54, DISPERSE YELLOW 82, DISPERSE RED 60, DISPERSE RED 375, DISPERSE VIOLET 17, DISPERSE RED 4, DISPERSE RED 11, DISPERSE BLUE 60, DISPERSE BLUE 359, DISPERSE BLUE 14, DISPERSE BLUE 3, DISPERSE BLUE 72, and DISPERSE BLUE 56.

12. The composition according to claim 10, wherein the pigment is at least one of: carbon black, graphite, vitreous carbon, activated charcoal, activated carbon, anthraquinone, phthalocyanine blue, phthalocyanine green, diazos, monoazos, pyranthrones, perylene, quinacridone, and indigoid pigments.

13. The composition according to claim 1, wherein an amount of the colorant is in a range of 0.1–20 parts by weight with respect to 100 parts by weight of the composition.

14. The composition according to claim 1, wherein an amount of the colorant is in a range of 0.5–15 parts by weight with respect to 100 parts by weight of the composition.

15. The composition according to claim 10, further including an acid or a base to increase solubility of the disperse dye in a solvent and stabilize the dispersion of the pigment.

16. The composition of claim 1, wherein the 2-methoxyphenol derivative has a formula of (4):

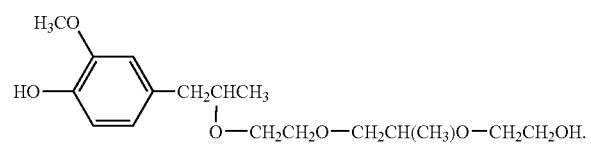

(4)

17. The composition of claim 1, wherein the 2-methoxyphenol derivative has a formula of (8):

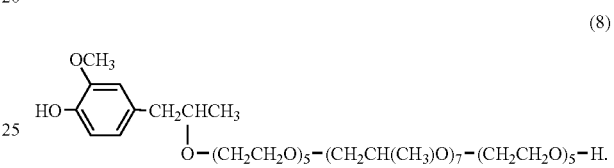

(8)

18. The composition of claim 1, wherein the 2-methoxyphenol derivative has a formula of (12):

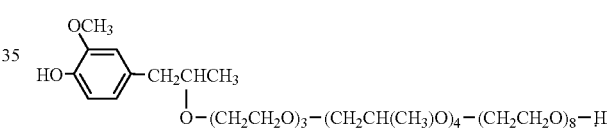

(12)

* * * * *

UNITED STATES PATENT AND TRADEMARK OFFICE
CERTIFICATE OF CORRECTION

| | |
|---|---|
| PATENT NO. | : 7,223,805 B2 |
| APPLICATION NO. | : 10/724753 |
| DATED | : May 29, 2007 |
| INVENTOR(S) | : Yeon-Kyoung Jung et al. |

It is certified that error appears in the above-identified patent and that said Letters Patent is hereby corrected as shown below:

Column 14, Line 26, change "-$(CH_2CH_2O)_a(CH_2CH(CH_3)O)_b(CH_2CH_2O)_c$-H" to --$(CH_2CH_2O)_a(CH_2CH(CH_3)O)_b$-$(CH_2CH_2O)_c$-H--.

Signed and Sealed this

Thirtieth Day of October, 2007

JON W. DUDAS
*Director of the United States Patent and Trademark Office*